United States Patent [19]

Paulus

[11] 4,444,878
[45] Apr. 24, 1984

[54] BISPECIFIC ANTIBODY DETERMINANTS

[75] Inventor: Henry P. Paulus, Boston, Mass.

[73] Assignee: Boston Biomedical Research Institute, Inc., Boston, Mass.

[21] Appl. No.: 332,881

[22] Filed: Dec. 21, 1981

[51] Int. Cl.³ .................. G01N 33/54; C12M 1/40; C12M 1/34; C12N 11/02; C12N 11/12; C12N 11/18; C12N 9/96; C12Q 1/26; C12Q 1/28; C12Q 1/34

[52] U.S. Cl. .......................... 435/7; 435/18; 435/25; 435/28; 435/175; 435/177; 435/179; 435/188; 435/288; 435/291; 435/805; 435/810; 435/817; 436/512; 436/518; 436/528; 436/530; 436/548; 436/808; 436/819; 204/403; 422/55

[58] Field of Search ............ 435/7, 18, 25, 28, 174, 435/175, 178, 179, 288, 291, 172, 188, 805, 810, 817, 177, 4; 436/548, 806, 528, 530, 512, 518, 808, 819; 204/195 B; 260/112 R; 422/55, 57

[56] References Cited

U.S. PATENT DOCUMENTS

| | | | |
|---|---|---|---|
| 4,193,982 | 3/1980 | Avrameas et al. | 436/512 |
| 4,200,436 | 4/1980 | Mochida et al. | 435/7 |
| 4,208,479 | 6/1980 | Zuk et al. | 436/512 |
| 4,223,005 | 9/1980 | Teodorescu et al. | 435/7 |
| 4,235,869 | 11/1980 | Schwarzberg | 435/7 |
| 4,240,889 | 12/1980 | Yoda et al. | 435/817 |
| 4,278,761 | 7/1981 | Hastings et al. | 435/178 |
| 4,298,685 | 11/1981 | Parikh et al. | 435/810 |
| 4,331,647 | 5/1982 | Goldenberg | 424/9 |
| 4,340,535 | 7/1982 | Voisin et al. | 260/112 R |
| 4,350,626 | 9/1982 | Masuho et al. | 260/112 R |
| 4,376,110 | 3/1983 | David et al. | 435/7 |

FOREIGN PATENT DOCUMENTS

| | | |
|---|---|---|
| 68763 | 1/1983 | European Pat. Off. . |
| 50-155678 | 12/1975 | Japan ................ 435/7 |

OTHER PUBLICATIONS

Hämmerling et al., J. Exp. Med. 128:1461–1469, (1968).
Bergmeyer, Methods of Enzymatic Analysis, vol. 3, Academic Press, Inc., New York, 1180–1184, (1974).
Karube et al., Biochem. Biophys. Res. Comm., vol. 47, pp. 51–54, (1972).
Nisonoff et al., (1964), Science 134, 376–379.
Nisonoff et al., (1960), Arch. Biochem. Biophys. 89, 230–244.
Nisonoff and Rivers, (1960), Arch. Biochem. Biophys. 93, 460–462.
Nisonoff, (Nov. 2, 1981), Current Contents 44, 25.
Raso and Griffin, (1978), Fed. Proc. 37, 1350.
Milstein, (1981), Proc. R. Soc. Lond. B211, 393–409.
Schwaber et al., (1974), P.N.A.S. USA 71, 2203–2207.
Cotton et al., (1973), Nature 244, 42–43.
Raso et al., (1981), Cancer Research 41, 2073–2078.
Rechnitz, (1981), Science 214, 287–291.
Galfre et al., (1981), Methods in Enzymology 73, 3–46.
Ey et al., (1978), Immunochemistry 15, 429–436.
Hackett et al., (1981), Immunology 4, 207–215.
Raso and Griffin, (1980), J. Immunol. 125, 2610–2616.
Satoh et al., (1976), Biotechnol. and Bioengineering 18, 269–272.
Cuatrecasas et al., (1968), Proc. Nat'l. Acad. Sci. USA 61, 636–643.
Bayer et al., (1974), Methods in Enzymology 34B, 265–267.

Primary Examiner—Esther M. Kepplinger

[57] ABSTRACT

A homogenous sample of identical bispecific antibody determinants, each determinant being composed of two L-H half-molecules linked by disulfide bonds, each L-H half-molecule being specific for a different antigenic determinant and including at least the F(ab')₂ portion of a monoclonal IgG antibody. The bispecific antibody determinant and including at least the F(ab') portion of tilamellar assemblies and enzyme electrodes.

6 Claims, 5 Drawing Figures

BISPECIFIC ANTIBODY DETERMINANTS

The IgG antibodies are known to consist of two half-molecules, each consisting of a light (L) chain and a heavy (H) chain. The H chains of the two halves are linked by disulfide bonds, which can be broken by selective reduction. If this step is performed for two different IgG samples, the half-molecules can be combined to form hybrid antibodies. This has been accomplished using intact rabbit globulins; Nisonoff et al. (1964) Science 134, 376–379.

Hybrids have also been formed using the F(ab')$_2$ fragments of IgG antibodies, rather than intact antibodies; i.e., the F(c) portions of the molecules, which do not provide immunospecificity, are, prior to hybridization, removed by digestion with an appropriate protease such as papain. This procedure has been described in Nisonoff et al. (1960) Arch. Biochem. Biophys. 89, 230–244 and in Nisonoff and Rivers (1960) Arch. Biochem. Biophys. 93, 460–462. In a later discussion of the first paper Nisonoff wrote, in Current Contents (Nov. 2, 1981) 44, 25:

> So far this procedure has had limited application, principally in the staining of cell surfaces with ferritin by using a hybrid of anti-ferritin antibody and antibody to a cell surface antigen. The use of hybrid antibody has also been considered as a means of bringing a pharmacological agent specifically into contact with a desired tissue surface.

The use of such hybrids for the delivery of cytotoxic drugs has also been suggested in Raso and Griffin (1978) Fed. Proc. 37, 1350.

Milstein (1981) Proc. R. Soc. Lond. B211, 393–412 suggests the possibility of using "monoclonal antibodies as carriers of toxic substances for specific treatment of tumors," and states that "(i)t is possible that Fab fragments will be better targeting agents than intact antibody."

Hybrid antibodies have also been formed by fusing two cells, each capable of producing different antibodies, to make a hybrid cell capable of producing hybrid antibodies. Such a method is described in Schwaber et al. (1974) P.N.A.S. U.S.A. 71, 2203–2207, Mouse myeloma cells were fused to human lymphocytes, and the resultant fused cells produced "hybrid antibody molecules containing components of mouse immunoglobulins assembled with human heavy and light chains." The human antibody component was not monoclonal, and was undefined.

Schwaber et al. also describes an in vitro experiment in which the mouse and human antibodies were reduced strongly enough to break bonds between L and H chains, and then "allowed to recombine randomly."

In Cotton et al. (1973) Nature 244, 42–43 there is described an experiment in which mouse myeloma cells were fused to rat tumor cells to produce fusions which produced "an extra component" which was "likely . . . a hybrid mouse-rat light chain dimer" as well as "non-symmetrical molecules made up of one light chain of each parental type."

Another paper, Raso et al. (1981) Cancer Research 41, 2073–2078, describes the formation of an impure sample of rabbit antibody F(ab')$_2$ fragments against human IgG F(ab')$_2$ fragments; the rabbit antibody fragments were split by reduction and reassembled with antiricin A chain F(ab') fragments. The dual specificity dimers were used in targeted drug delivery experiments. The article states:

> The 2 types of purified antibodies used for this work were isolated from conventional heteroantisera. Thus, a complicated array of affinity and specificity combination must arise upon annealing these 2 populations. The advent of homogeneous hybridoma-derived antibodies will afford absolute control over the binding affinities of the constituent halves of a hybrid antibody, and this uniformity should greatly boost their ultimate effectiveness as delivery vehicles.

The present invention provides a homogeneous sample of identical bispecific antibody determinants, each bispecific determinant being composed of two L-H half molecules linked by disulfide bonds, each L-H half molecule being different from the other and being specific for a different antigenic determinant, and being composed of at least the F(ab') portion of a monoclonal IgG antibody.

The bispecific antibody determinants of the invention are made according to the following procedure. Using conventional methods, two different monoclonal IgG antibody samples are produced, each antibody having one of two desired specificities. If desired, each sample is then exposed to an appropriate protease such as papain to cleave off the F(c) portion of the antibody molecules to produce F(ab')$_2$ fragments. Each sample is then subjected to conditions sufficient to break at least some of the disulfide bonds linking the L-H half-molecules so that at least some of the antibodies are split into two half-molecules.

The two samples are then combined under conditions which permit at least some half-molecules of each determinant to chemically combine with at least some half-molecules of the other determinant to form the bispecific antibody determinants of the invention.

The bispecific antibody determinants molecules are then separated from the rest of the mixture. One separation method is contacting the mixture with an affinity matrix containing an antigen capable of specifically binding to either of the two halves of the bispecific antibody determinant, then eluting bound matrix-bound material, and contacting that material with an affinity matrix containing an antigen capable of specifically binding the other half-molecule. The material bound to this second matrix has the required dual specificity.

An alternative separation method can be used in a case where one of the halves of the bispecific antibody determinant has a specificity for an antigenic determinant which is a macromolecule (a molecule having a molecular weight greater than about 1000 daltons). This method involves adding the macromolecular antigenic determinant to the sample containing the bispecific antibody determinant to be purified to form immune complexes which can be separated into subfractions having different molecular weights by, e.g., gel filtration or electrophoresis. The subfraction having a molecular weight equivalent to the molecular weight of the complex of the desired bispecific antibody determinant with the macromolecular antigen is separated from the other subfractions, and, if desired, the macromolecular antigen is then removed using conventional methods.

Figure 1:
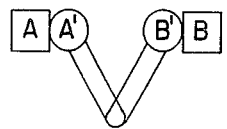
FIG. 1 is a diagrammatic representation of two different antigenic determinants linked by a bispecific antibody determinant.

The bispecific antibody determinants of the invention are useful for a wide range of applications. Referring to FIG. 1, these applications all flow from the ability of these determinants to serve as highly specific linkers through specific sites A' and B', of any two antigenic determinants A and B capable of stimulating antibody production in animals; e.g., effective proteins, polypeptides, carbohydrates, nucleic acids, or haptens, either free or immobilized on surfaces or particles.

One application of the bispecific antibody determinants of the invention is their use as agents for bonding a desired antigenic entity to a desired surface which has a different antigenic determinant immobilized on it. For example, enzymes so immobilized on particles or membranes can be used as solid-state catalysts. Advantages of this type of immobilization over others are that antibodies can be selected which have no adverse effect on enzyme activity, and that pure enzymes can be immobilized from impure mixtures. Bispecific antibody determinants can also be used as highly specific bispecific reagents for immunoassay procedures which are used, e.g., in the diagnosis of medical disorders, or as molecular probes to study the relationships between antigenic determinants in biological systems.

An additional application of the bispecific antibody determinants is their use in electrodes. Currently-used enzyme electrodes frequently employ tissue slices as the enzyme source. For example, electrodes for measuring glutamine have been made using a conventional $NH_3$ electrode in combination with kidney slices as the source of glutaminase, the enzyme which breaks down glutamine to produce measurable $NH_3$ ions; Rechnitz (1981) Science 214, 287–291.

The present invention provides electrode apparatus for the measurement in a sample of an unknown amount of a substance which is acted on by one or more enzymes to evolve a measurable ion or compound, the ion or compound evolved being a measure of the unknown substance. The electrode apparatus includes means for measuring the measurable ion or compound, and, associated with that means, a membrane having associated therewith a plurality of molecules of each enzyme which acts on the substance to be measured and, bonded to the molecules of each enzyme, a plurality of identical, bispecific antibody determinants. Each determinant is composed of two different L-H half-molecules linked by disulfide bonds, and each half-molecule includes at least the F(ab') portion of a monoclonal IgG antibody. One said L-H half-molecule is specific for an antigenic site on the enzyme molecule to which it is bonded and the other half-molecule is specific for an antigenic determinant on the membrane to which the bispecific antibody determinant is bonded to become immobilizably associated with the membrane.

The electrode can be used to measure any substance which can be metabolized by an enzyme or combination of enzymes in a way which produces or consumes a measurable ion or compound such as $NH_3$, $CO_2$, $O_2$, or $H^+$, provided that each enzyme can bind specifically to a site on an immobilized bispecific antibody determinant.

Figure 2:
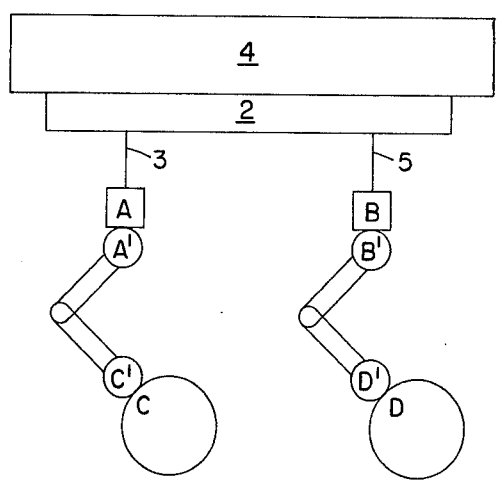
FIGS. 2 and 3 are diagrammatic representations of electrodes employing bispecific antibody determinants.
Figure 3:
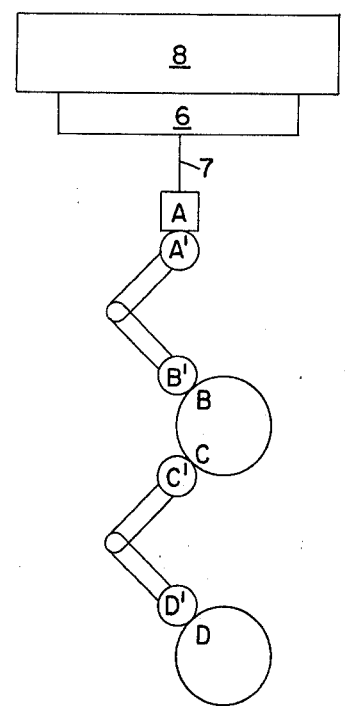

The reaction can be one which requires more than one enzyme. It is required in such a case that all of the required enzymes be immobilized on bispecific antibody determinants which are immobilized in the electrode. FIGS. 2 and 3 illustrate two modes of enzyme immobilization in a two-enzyme system in which the two enzymes catalyze consecutive reactions in the conversion of a substance to an ion or compound which can be measured by the appropriate ion or compound-specific membrane electrode.

Referring to FIG. 2, membrane 2 of electrode 4 bears, on spacer arms 3 and 5, different haptens A and B, in the desired ratio, to which are immobilized different bispecific antibody determinants having, respectively, hapten-specific sites A' and B'. The second site on each bispecific antibody determinant is specific, respectively, for binding sites on enzymes C and D, which catalyze consecutive steps in the breakdown of the substance to be measured into a measurable compound or ion.

Figure 4:
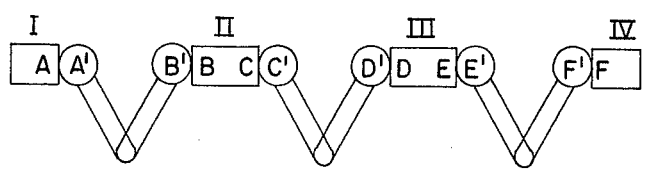
FIG. 4 is a diagrammatic representation of a self-assembling network employing bispecific antibody determinants.

Referring to FIG. 3, membrane 6 of electrode 8 bears, on spacer 7, hapten A, to which is immobilized a bispecific antibody determinant having hapten A-specific site A' and a second site, B', which is specific for binding site B on one of the two enzymes necessary for the breakdown of the substances to be measured into a measurable compound or ion. The second bispecific antibody determinant has a site, C', specific for antigenic binding site C on the first enzyme, and a second site, D', specific for a different antigenic binding site D on the second enzyme required for the production of the measurable compound or ion. The advantage of the arrangement shown in FIG. 4 is that it assures that the two enzymes are closely linked so that the two reactions are efficiently coupled.

Enzyme electrodes made using bispecific antibody determinants possess several advantages over conventional enzyme electrodes. One advantage is their precise self-assembling property: the desired electrode assembly is generated simply by attaching the appropriate hapten or haptens to the membrane (either the electrode membrane or a separate membrane associated with the electrode) and then immersing the hapten-derived membrane into a solution containing the appropriate bispecific antibodies and enzymes. This ease of assembly also means that the electrode can be easily recharged after deterioration has occured through prolonged use.

Another advantage of the electrodes is also a function of the specificity of the bispecific antibody determinants. Any given enzyme will possess a number of antigenic sites capable of binding to a specific site of an antibody. However, coupling at many of these sites can cause inactivation of the enzyme. In the case of bispecific monoclonal antibody determinants, this problem is avoided because the determinants are selected so that they couple with the enzyme only at a site which does not cause deactivation of the enzyme.

A further advantage is that assembly or recharging of the electrode can be done with impure enzyme mixtures because the unique specificity of the bispecific antibody determinants assures the selection of the proper enzymes from the impure mixture.

In some instances the membrane containing the immobilized enzymes can be covered with a second semipermeable membrane to slow the deterioration of the electrode assembly, or the assembly can be stabilized by treatment with glutaraldehyde.

Yet another application for the bispecific antibody determinants is their use in the formation of self-assembling networks for use, e.g., as molecular microcircuits. Such a network is illustrated diagrammatically in FIG. 4, wherein A, B, C, D, E, and F represent antigenic determinants and A', B', C', D', E', F', represent, respectively, corresponding antibody determinants. It can be seen that the number of linked specific determinants is virtually limitless and, further, that the network can be highly complex and in two or three dimensions. Most importantly, the network, no matter how complex, is entirely self-assembling in a uniquely defined way.

One example of such a self-assembling network is a multilamellar assembly for use, e.g., in chemical assays or in the production of specific chemicals in industrial processes. Currently used assemblies for assays of substances in, e.g., serum, employ a series of layers of enzymes trapped between membranes of low porosity. The sample containing the substance to be measured is placed on the outer surface of the assembly and allowed to seep down through the layers, interacting successively with the trapped enzymes until, in the bottom layers, measurable result is produced, e.g. a fluorescence or a color change; this result is a measure of the substance being measured in the sample.

The multilamellar assembly of the invention employs bispecific antibody determinants to link two or more enzymes which can be sequentially acting, as illustrated in FIG. 4 (I-IV representing different enzymes). The low-porosity membranes of current assemblies are thus in many instances unnecessary, the spatial relationships among the enzymes already being fixed by their attachment to bispecific antibody determinants. Furthermore, the use of bispecific antibody determinants to link enzymes enhances the efficiency of the reaction by reducing the diffusion time of intermediates.

In the multilamellar assemblies of the invention, the antigenic determinants linked by the bispecific antibody determinants are, in some cases, not enzymes but other catalysts e.g., microbial cells. This will be the case in certain industrial processes, for example, in which the goal of the process is not the measurement of a compound but the production of a desired chemical via a series of chemical reactions.

The following specific examples are intended to more particularly point out the invention, without acting as limitations upon its scope.

EXAMPLE 1

The following procedure is used to prepare a homogeneous sample of identical bispecific antibody determinants in which each bispecific determinant has a site specific for a unique antigenic site on the enzyme glucose oxidase, and a site specific for a unique antigenic site on the enzyme $\beta$-galactosidase.

The first step is the preparation of monoclonal antibodies against the two enzymes glucose oxidase and $\beta$-galactosidase. This is done by first immunizing one group of BALB/C mice against each enzyme using standard immunization procedures.

Following immunization, spleen cells of immunized animals are prepared and fused with a derivative of MOPC-21 myeloma cells (SP2/O-Ag14) using the procedure described in Galfre et al. (1981) Methods in Enzymology 73, 3-46. The hybrid cells are selected in hypoxanthine-aminopterin-thymidine medium, cloned, and screened for production of antibodies against the desired enzymes by the method described in Galfre et al. Id. The clones found to produce antibodies against the desired enzyme are then screened to select a clone which produces an antibody of the IgG class which has a high affinity for the enzyme and which does not cause inactivation of the enzyme. The clones of interest are stored until use under liquid nitrogen. Antibody is prepared by propagating the cloned cells in spinner flasks in Dulbeccos's modified Eagles' medium containing 5% fetal calf serum. Alternatively, a higher antibody yield is obtained by the standard technique of growing the cells as ascitic tumors in the peritoneal cavities of pristane-primed mice.

The desired IgG antibodies against glucose oxidase and $\beta$-galactosidase are then purified from medium or ascites fluid by affinity chromatography on protein A-Sepharose, as described in Ey et al. (1978) Immunochemistry 15, 429-436. Each of the two purified antibodies is then converted to F(ab') fragments by treatment with pepsin according to the procedure of Hackett et al. (1981) Immunology 4, 207-215, as follows. Four mg of purified immunoglobulins (IgG), dissolved in 0.1 M acetate buffer, pH 4.6, are incubated with 40 $\mu$g of pepsin at 37° C. After 20 hours, the mixture is adjusted to pH 8.1 with Tris buffer, passed through a column of protein A-Sepharose, and then purified by gel filtration on Sephadex G-50.

The two types of F(ab') fragments are then combined to form bispecific determinants, as follows. First, one (either one) of the fragments is subjected to mold reduction with 10 mM mercaptoethylamine hydrochloride at 37° C. for 1 hour under a nitrogen atmosphere to separate the fragment into half-molecules without breaking the bonds between H and L chains. The reducing agent is then removed by passing the mixture through a column of Dowex-50 at pH 5. The effluent is then reacted immediately with 2 mM 5,5'-dithiobis (2-nitrobenzoic acid) in 0.02 M Na phosphate, pH 8.0, and 3 mM EDTA, as described in Raso and Griffin, J. Immunol. (1980) 125, 2610-2616. The Fab'-thionitrobenzoate derivative thus formed is then purified by gel filtration on Sephadex G-100 in 0.2 M Na phosphate, pH 8.0. The other F(ab')$_2$ fragment is likewise reduced and treated with Dowex-50, and the resulting Fab' derivative is mixed immediately with an equimolar amount of the Fab'-thionitrobenzoate derivative and incubated for 3 h at 20° C. to form a mixture containing a high yield of identical bispecific antibody determinants, each determinant being made up of two F(ab') L-H half molecules linked by disulfide bonds. To obtain a homogeneous sample of the identical bispecific antibody determinants, the mixture is passed through a column of Sepharose 4B equilibrated with 0.1 M Tris, pH 7.5, the Sepharose having covalently bonded to it $\beta$-galactosidase. The column is then washed with 0.1 M Tris, pH 7.5, and the anti-$\beta$-galactosidase determinants are then eluted with 0.1 M glycine, pH 2.5, and then neutralized with Tris.

The eluate is then passed through a second column of Sepharose 4B which has glucose oxidase covalently bonded to it by CNBr activation. The column is washed with 0.1 M Tris, pH 7.5, and the bispecific anti-glucose oxidase, anti-$\beta$-galacotosidase determinants are then eluted with 0.1 M glycine pH 2.5, and then neutralized with Tris. The eluate constitutes a homogeneous sample of the desired identical bispecific antibody determinants.

EXAMPLE 2

Using the same procedure employed in Example 1, a homogeneous sample of identical bispecific antibody determinants is prepared in which one antibody site is specific for a different antigenic site on the enzyme glucose oxidase from the site for which the bispecific antibody determinant of Example 1 is specific, and in which the second antibody site is specific for an antigenic site on Type I collagen.

EXAMPLE 3

An enzyme electrode for the measurement of lactose is constructed according to the following procedure. First, a collagen membrane shaped to fit over a commercial $O_2$ electrode is prepared by electrolysis of a collagen fibril suspension using platinum electrodes, as described in Karube et al. (1972) 47, 51–54 BBRC.

A solution is prepared of the bispecific antibody determinants from Example 2 together with a 10-fold or higher molar excess of glucose oxidase, in 0.1 M phosphate buffer, pH 7.0; the glucose oxidase need not be pure. The collagen membrane is immersed in this solution and incubated for 1 h at 20° C., after which time it is rinsed with buffer and then transferred to a solution containing the antibody from Example 1 together with a 10-fold or higher molar excess of $\beta$-galactosidase in 0.1 M phosphate buffer, where it is incubated at 20° C. for 1 h. The membrane is then quickly rinsed in buffer and stabilized by immersion in 0.5% glutaraldehyde in 0.1 M phosphate buffer, pH 7.0, for 3 minutes.

The membrane is then placed over the oxygen-permeable teflon membrane of the commercial $O_2$ electrode, rendering the electrode ready for use for the measurement of lactose, in a manner analogous to the method of measuring sucrose described in Satoh et al. (1976) Biotechnol. and Bioengineering 18, 269–272. A sample containing an unknown amount of lactose is contacted with the membrane, and the immobilized $\beta$-galactosidase catalyzes the breakdown of the lactose into glucose, which is then acted on by the immobilized glucose oxidase to release $O_2$, which is measured as a measure of lactose in the sample.

In the preparation of the membrane described above, molar excesses of enzyme over antibody are employed because $\beta$-galactosidase and glucose oxidase are each composed of several identical subunits. An excess of enzyme assures that, on average, only a single antigenic site on each enzyme molecule is involved in complex formation. In the preparation of other electrode using monomeric enzymes, molar excesses of enzymes are not necessary. When equimolar amounts of enzymes and bispecific antibody determinants are used, the reaction can be allowed to proceed in a single stage.

EXAMPLE 4

The following is a description of an example of the type of assay assembly which employs the production of a colored or fluorescent substance, which can be measured colorimetrically, reflectometrically, or fluorometrically, as a measure of an unknown amount of a substance being assayed.

Figure 5:
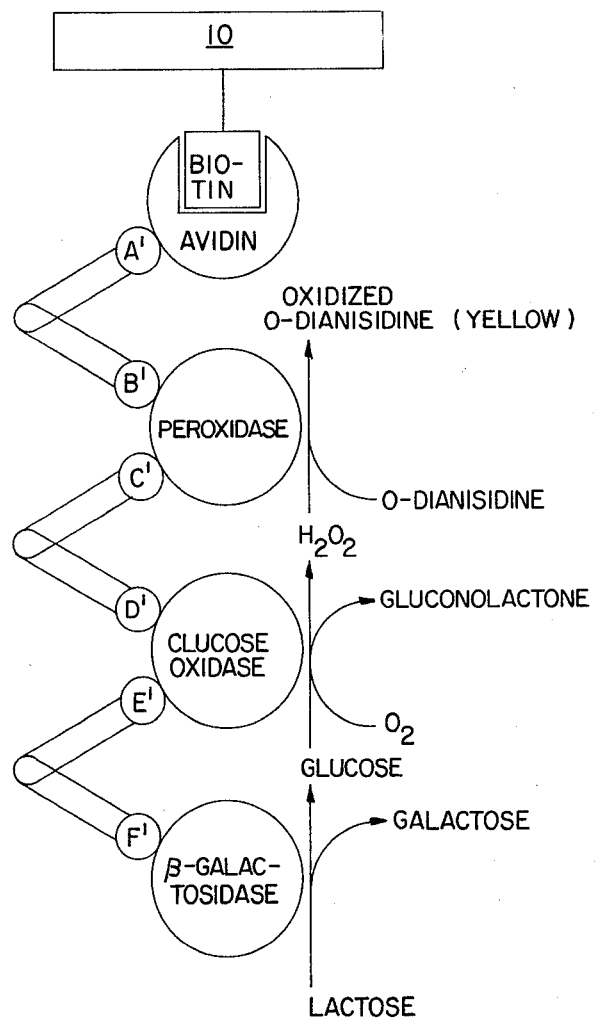
FIG. 5 is a diagrammatic representation of a multilamellar assembly useful for an assay method.

FIG. 5 is a diagrammatic representation of a colorimetric indicator for lactose. Biotin-substituted regenerated cellulose membrane 10 is used as the support for the immobilized enzymes which participate in the series of reactions by which lactose in a sample generates $H_2O_2$ to produce a colorimetrically measurable result, which is a measure of the amount of lactose in the sample.

The enzymes are immobilized, as shown in FIG. 5, by being bonded to three different bispecific antibody determinants, prepared according to the procedure described in Example 1. The first determinant has one site, A', specific for an antigenic site on the protein avidin, and the other site, B', specific for an antigenic site on the enzyme horseradish peroxidase. The second determinant has a site, C', specific for a different antigenic site on horseradish peroxidase, and the second site, D', specific for an antigenic site on glucose oxidose. The third determinant has an antibody site E', specific for a different antigenic site on glucose oxidase, and the second site, F', specific for an antigenic site on $\beta$-galactosidase.

Substituted cellulose membrane 10 is prepared by the cyanogen bromide procedure, e.g. Cuatrecasas et al. (1968) Proc. Nat'l. Acad. Sci. U.S.A. 61, 636–643, as follows. Regenerated cellulose membranes are suspended in 0.1 M $NaHCO_3$ at 4° C. and treated with an equal volume of 2.5% CNBr solution, the pH being continuously adjusted to 11 with 2 N NaOH and the temperature kept at 4° C. After 8 min, the cellulose membranes are washed with 0.1 M $NaHCO_3$ and then with water, 50% acetone, and finally with 100% acetone. The cellulose membranes are then incubated at 4° C. for 20 h in 0.2 M $NaHCO_3$, pH 9, containing 1 mg per ml of $\epsilon$-N-biotinyl-L-lysine (Bayer et al. (1974) *Methods in Enzymology* 34B, 265–267), followed by extensive washing with water.

The biotin-substituted cellulose membrane is then immersed in 0.1 M phosphate buffer, pH 7.0, and incubated for 1 h at 20° C. with approximately equivalent molar amounts of avidin, horseradish peroxidase, and the bispecific antibody determinant having sites A' and B'. The membrane is then rinsed with buffer and transferred to a solution containing an approximately equivalent molar amount of the bispecific antibody determinant having sites C' and D', and a 10-fold molar excess of glucose oxidase. After 1 hour at 20° C., the membrane is rinsed with buffer and transferred to a solution containing an approximately equivalent molar amount of the bispecific antibody determinant having sites E' and F', and a 10-fold molar excess of $\beta$-galactosidase, and incubated at 20° C. for 1 h, followed by rinsing with buffer. If repeated use is anticipated, the membrane is stabilized by immersion in 0.5% glutaraldehyde in 0.1 M phosphate buffer, pH 7, for 3 min.

The enzymes used in the above-described procedure need not be pure. In the example described, a molar excess of $\beta$-galactosidase and glucose oxidase was necessary because these enzymes are composed of several identical subunits. In cases where only monomeric enzymes are used, molar excesses of enzymes are not necessary. When equimolar amounts of enzymes and bispecific antibody determinants are used, the reaction can be allowed to proceed in a single stage.

For the determination of lactose, membrane 10 is immersed in or wetted with a sample containing an unknown amount of lactose in 0.1 M phosphate buffer, pH 7, and 0.01% o-dianisidine.

As shown in FIG. 5, lactose in the sample first acts on $\beta$-galactosidose to form glucose, which in turn is acted on by glucose oxidase, in the presence of oxygen, to release $H_2O_2$, which, with peroxidase, oxidizes o-dianisidine to produce a yellow dye with absorbance at 460 NM. Various other chromogenic or fluorogenic substances can be substituted for o-dianisidine.

What is claimed is:

1. A homogenous sample of identical bispecific antibody determinants, each said determinant comprising two L-H half-molecules linked by disulfide bonds, each said L-H half-molecule being specific for a different antigenic determinant, and comprising at least the F(ab') portion of a monoclonal IgG antibody, one said antigenic determinant comprising an antigenic site on a solid matrix, whereby said bispecific antibody determinant is capable of being immobilized on said solid matrix by binding to said matrix at said antigenic site, said sample comprising a multilamellar assembly wherein said antigenic site on said matrix is a site on a haptenic molecule attached to said matrix, said bispecific antibody determinant is bonded to said haptenic molecule, the other said antigenic determinant comprises a first antigenic site on a first protein molecule, said bispecific antibody determinant being bonded to said protein molecule, and there is bonded to said first protein molecule, at a second antigenic site on said protein molecule, a second bispecific antibody determinant different from the determinant bonded to said haptenic molecule, each said second determinant comprising two L-H half molecules linked by disulfide bonds, each said L-H half molecule being specific for a different antigenic determinant, one said antigenic determinant being a second antigenic site on said first protein molecule, each said half-molecule comprising at least the F(ab') portion of a monoclonal IgG antibody.

2. The assembly of claim 1 wherein the other said antigenic determinant for which said second bispecific antibody determinant is specific is an antigenic site on a second protein molecule.

3. The assembly of claim 2 wherein each said first and second protein is an enzyme.

4. The assembly of claim 3 wherein said assembly is useful for the measurement of a substance, and said enzymes participate in a series of reactions which result in the production, from said substance, of a measurable effect which is a measure of said substance.

5. Electrode apparatus for the measurement in a sample of an unknown amount of a substance which is acted on by one or more enzymes to evolve a measurable ion or compound, said ion or compound evolved being a measure of said unknown substance, said electrode apparatus comprising means for measuring said measurable ion or compound, and, associated with said means for measuring said measurable ion or compound, a membrane having associated therewith a plurality of molecules of each said enzyme which acts on said substance to be measured and, bonded to the molecules of each said enzyme, a plurality of identical, bispecific antibody determinants, each said determinant comprising two L-H half-molecules linked by disulfide bonds, each said half-molecule being different from the other and comprising at least the F(ab') portion of a monoclonal IgG antibody, one said L-H half-molecule being specific for an antigenic site on the enzyme molecule to which it is bonded, the other half-molecule being specific for an antigenic determinant on said membrane, said bispecific antibody determinant being bonded thereto, wherein said substance to be measured is acted on by more than one enzyme, and the molecules of at least one of said enzymes are bonded to half-molecule of each of two different said bispecific antibody determinants at two different antigenic sites on said enzyme molecules.

6. Electrode apparatus for the measurement in a sample of an unknown amount of a substance which is acted on by one or more enzymes to evolve a measurable ion or compound, said ion or compound evolved being a measure of said unknown substance, said electrode apparatus comprising means for measuring said measurable ion or compound, and, associated with said means for measuring said measurable ion or compound, a membrane having associated therewith a plurality of molecules of each said enzyme which acts on said substance to be measured and, bonded to the molecules of each said enzyme, a plurality of identical, bispecific antibody determinants, each said determinant comprising two L-H half-molecules linked by disulfide bonds, each said half-molecule being different from the other and comprising at least the F(ab') portion of a monoclonal IgG antibody, one said L-H half-molecule being specific for an antigenic site on the enzyme molecule to which it is bonded, the other half-molecule being specific for an antigenic determinant on said membrane, said bispecific antibody determinant being bonded thereto, wherein said substance to be measured is lactose, said enzymes are $\beta$-galactosidase and glucose oxidase, and said measurable compound is oxygen, wherein the molecules of said glucose oxidase are bonded to two different said bispecific antibody determinants at two different antigenic sites on said glucose oxidase molecules.

* * * * *

UNITED STATES PATENT AND TRADEMARK OFFICE
CERTIFICATE OF CORRECTION

PATENT NO. : 4,444,878
DATED : April 24, 1984
INVENTOR(S) : Henry P. Paulus

It is certified that error appears in the above-identified patent and that said Letters Patent are hereby corrected as shown below:

In the Abstract, line 5, "$F(ab')_2$" should be --$F(ab')$--;

In the Abstract, line 7, "determinant" should be plural; same line, delete "and including at least the $F(ab')$ portion of tilamellar" and insert instead --are useful, e.g., in the formation of multilamellar--;

Col. 5, line 23, "layers" should be --layer--;

Col. 6, line 19, "$F(ab')$" should be --$F(ab')_2$--;

Col. 6, line 28, "$F(ab')$" should be --$F(ab')_2$--;

Col. 6, line 30, "mold" should be --mild--;

Col. 8, line 67, "460 NM" should be --460 nm--.

Signed and Sealed this

Twenty-eighth Day of August 1984

[SEAL]

Attest:

GERALD J. MOSSINGHOFF

*Attesting Officer*     *Commissioner of Patents and Trademarks*

UNITED STATES PATENT OFFICE
CERTIFICATE OF CORRECTION

Patent No. 4,444,878         Dated April 24, 1984

Inventor(s) Henry P. Paulus

It is certified that error appears in the above-identified patent and that said Letters Patent are hereby corrected as shown below:

Claims 2, 3 and 4, line 1 of each claim, change "assembly" to --sample--.

Signed and Sealed this

Fifteenth Day of October 1985

[SEAL]

Attest:

Attesting Officer

DONALD J. QUIGG

Commissioner of Patents and Trademarks—Designate